United States Patent
Cottrell et al.

(10) Patent No.: US 7,335,613 B2
(45) Date of Patent: *Feb. 26, 2008

(54) FIBER SUBSTRATE WITH ANTIBACTERIAL FINISH AND METHODS OF MAKING AND USING THE SAME

(75) Inventors: Stephanie Nussbaum Cottrell, Denver, NC (US); Tirthankar Ghosh, Oreland, PA (US); Barry Weinstein, Dresher, PA (US)

(73) Assignee: Rohm and Haas Company, Philadelphia, PA (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/082,667

(22) Filed: Mar. 17, 2005

(65) Prior Publication Data

US 2005/0226914 A1 Oct. 13, 2005

Related U.S. Application Data

(60) Provisional application No. 60/560,675, filed on Apr. 8, 2004.

(51) Int. Cl.
*B32B 27/04* (2006.01)
*B32B 27/12* (2006.01)

(52) U.S. Cl. .................... 442/123; 442/153; 442/164; 442/327

(58) Field of Classification Search ................ 442/123
See application file for complete search history.

(56) References Cited

U.S. PATENT DOCUMENTS

| 4,104,227 A | 8/1978 | Boessler et al. |
| 5,945,032 A | 8/1999 | Breitenbach et al. |
| 6,153,210 A | 11/2000 | Roberts et al. |
| 6,296,863 B1 | 10/2001 | Trogolo et al. |
| 6,584,668 B2 | 7/2003 | Green et al. |
| 6,821,936 B2 | 11/2004 | Green et al. |
| 2003/0026914 A1 | 2/2003 | Green et al. |
| 2003/0044447 A1 | 3/2003 | Zanini et al. |
| 2003/0186955 A1 | 10/2003 | Vange et al. |
| 2004/0001880 A1 | 1/2004 | Bowler et al. |
| 2004/0106340 A1 | 6/2004 | Kreider et al. |
| 2004/0106341 A1 | 6/2004 | Vogt et al. |
| 2004/0151755 A1 | 8/2004 | Rathore et al. |
| 2004/0214490 A1 | 10/2004 | Kreider et al. |
| 2005/0035327 A1* | 2/2005 | Canada et al. .......... 252/182.15 |
| 2005/0037058 A1 | 2/2005 | Canada et al. |
| 2005/0227895 A1* | 10/2005 | Ghosh et al. ............... 510/383 |

FOREIGN PATENT DOCUMENTS

| EP | 0 331 528 A | 9/1989 |
| JP | 11035681 | 2/1999 |
| JP | H11-222402 | 8/1999 |
| JP | 2001-97806 | 4/2001 |
| JP | 2001 106961 | 4/2001 |
| WO | WO 02/30204 A | 3/2002 |

OTHER PUBLICATIONS

Miyazjima, et al., "On the Complexation of Ag(I) and Cu(II) ions with poly (N-vinylimidzaole)", Reactive and Functional 38 (1998) pp. 183-195.
Journal of Inorganic Biochemistry 1997, 68(1), pp. 39-44.
Melaiye, et al., Silver(I)-Imidazole Cyclophane gem-Diol Complexes, Journal of American Chemical Society, vol. 127, No. 7, pp. 2285-2291(2005).

* cited by examiner

*Primary Examiner*—Lynda Salvatore
(74) *Attorney, Agent, or Firm*—Thomas S. Deibert

(57) ABSTRACT

Treated fiber substrates and methods of making and using the same are disclosed. The disclosed treated fiber substrates provide persistent, durable, broad spectrum, antimicrobial activity. The treated fiber substrates may be used in a variety of materials to impart antimicrobial activity thereto.

19 Claims, No Drawings

FIBER SUBSTRATE WITH ANTIBACTERIAL FINISH AND METHODS OF MAKING AND USING THE SAME

CROSS REFERENCE TO RELATED PATENT APPLICATIONS

This is a non-provisional application of prior pending U.S. Provisional Application Ser. No. 60/560,675 filed on Apr. 08, 2004.

The present invention relates to fiber substrates having an antimicrobial finish. The present invention also relates to methods of applying such finishes to fiber substrates and to methods of using such treated fiber substrates.

Microorganisms exist all around us. The potential repercussions on human health presented by many such microorganisms have made antimicrobial formulations an ubiquitous part of commercial and residential cleaning and disinfection processes. Some such repercussions may include, for example, illnesses and skin infections attributed to *Staphylococcus aureus, Klebsiella pneumoniae*, yeast and other unicellular organisms that may be present and multiply rapidly in our clothing and other fabrics we come into contact with and use everyday. Many conventional antimicrobial compositions, however, are unsuitable for durable use on such fabric surfaces. As a result, there is a perceived need for antimicrobial compositions suitable for durable use on fabric surfaces.

One method proposed for durably applying inorganic microbicide compositions based on ion-exchange compounds such as zirconium phosphates, glasses and/or zeolites to fabrics is suggested by Kreider et al. in U.S. Patent Application Publication No. 2004/0214490 A1. Kreider et al. disclose fabric substrates having a surface, a portion of which is coated with a non-electrically conductive finish, wherein said finish comprises at least one silver-ion containing compound selected from the group consisting of silver zirconium phosphate, silver zeolite, silver glass, and any mixtures thereof, and at least one crosslinked binder material.

Conventional inorganic microbicide compositions based on ion-exchange compounds such as zirconium phosphates, glasses and/or zeolites typically exhibit processability challenges relative to the treatment of fabrics. For example, such inorganic microbicide compositions are difficult to uniformly apply across the surface of a fabric and do not exhibit an inherent affinity for the surface of the fabric. Moreover, conventional compositions containing metal ion based microbicides (e.g., silver based) frequently exhibit instabilities which cause them to discolor upon exposure to heat and/or sun light. Hence, these microbicides frequently cause the systems into which they are incorporated to undergo conspicuous changes in coloration. Thus, the use of these conventional compositions tends to be limited to systems for which such conspicuous changes in coloration can be tolerated.

Accordingly, there is a need for new inorganic microbicide compositions which exhibit antibacterial activity based on their metal ion content, but without the undesirable processing and stability problems often associated with conventional compositions incorporating such metal ions.

In one aspect of the present invention, there is provided a treated fiber substrate having a surface, wherein at least a portion of the surface is treated with a finish, wherein the finish comprises at least one antimicrobial composition comprising a metal complexed with a polymer, wherein the metal is selected from copper, silver, gold, tin, zinc and combinations thereof; and, wherein the polymer comprises monomer residues selected from residue A, residue B, residue C and combinations thereof; with the proviso that the polymer contains no more than 99.5 wt % of monomer residues of residue B;

wherein residue A is

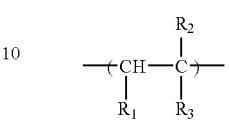

wherein residue B is

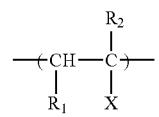

wherein residue C is

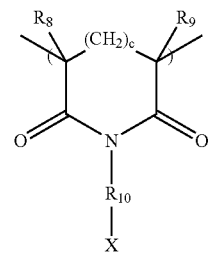

wherein

X is an unsaturated or aromatic heterocycle having at least one hetero atom selected from N, O and S;

c is 0 or 1;

$R_1$ is selected from H, $CH_3$ and $-CO_2R_4$; where $R_4$ is selected from H, $CH_3$, $C_2H_5$, a $C_3$-$C_{24}$ alkyl;

$R_2$ is selected from H, $CH_3$, $C_2H_5$, phenyl, $-CH_2CO_2R_5$ and $-CO_2R_5$; where $R_5$ is selected from (I)-(V),

H; (I)

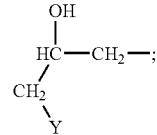  (II)

$-(CH_2CH(R_{11})O)_nH$; (III)

$-(CH_2CH(R_{11})O)_nCOCH_2COCH_3$; and, (IV)

$$\begin{array}{c} OH \\ | \\ HC-CH_2- \\ / \\ CH_2 \\ \backslash \\ Y \end{array}$$ (V)

where $R_{11}$ is selected from H, methyl and phenyl; n is an integer from 1 to 20; Y is selected from OH, $SO_3Z$ and X; where Z is selected from H, sodium, potassium and $NH_4^+$;

with the proviso that when the polymer contains 0 wt % of monomer residues of residue B and 0 wt % of monomer residues of residue C, $R_2$ is —$CH_2CO_2R_5$ or —$CO_2R_5$, $R_5$ is (V) and Y is X;

$R_3$ is selected from H, methyl, phenyl, sulfonated phenyl, phenol, acetate, hydroxy, a fragment O—$R_1$, where $R_1$ is as defined previously, —$CO_2R_{12}$ and —$CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;

$R_8$ and $R_9$ are independently selected from hydrogen, methyl, ethyl and $C_3$-$C_4$ alkyl;

$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly ($C_2$-$C_4$ alkylene)$_b$ oxides; where b is an integer from 2 to 20.

In another aspect of the present invention, there is provided a process for producing a treated fiber substrate comprising:

providing a fiber substrate;

providing a finish comprising at least one antimicrobial compound comprising a metal complexed with a polymer; wherein the metal is selected from copper, silver, gold, tin, zinc and combinations thereof; and, wherein the polymer comprises monomer residues selected from residue A, residue B, residue C and combinations thereof; with the proviso that the polymer contains no more than 99.5 wt % of monomer residues of residue B;

wherein residue A is

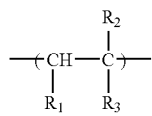

wherein residue B is

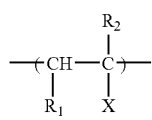

wherein residue C is

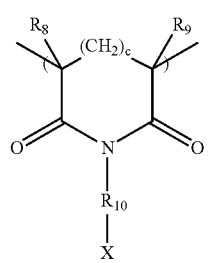

wherein
X is an unsaturated or aromatic heterocycle having at least one hetero atom selected from N, O and S;
c is 0 or 1;
$R_1$ is selected from H, $CH_3$ and —$CO_2R_4$; where $R_4$ is selected from H, $CH_3$, $C_2H_5$, a $C_3$-$C_{24}$ alkyl;

$R_2$ is selected from H, $CH_3$, $C_2H_5$, phenyl, —$CH_2CO_2R_5$ and —$CO_2R_5$; where $R_5$ is selected from (I)-(V), (I)

H;

(II)

(III)

—$(CH_2CH(R_{11})O)_nH$;

(IV)

—$(CH_2CH(R_{11})O)_nCOCH_2COCH_3$; and, (V)

where $R_{11}$ is selected from H, methyl and phenyl; n is an integer from 1 to 20; Y is selected from OH, $SO_3Z$ and X; where Z is selected from H, sodium, potassium and $NH_4^+$; with the proviso that when the polymer contains 0 wt % of monomer residues of residue B and 0 wt % of monomer residues of residue C, $R_2$ is —$CH_2CO_2R_5$ or —$CO_2R_5$, $R_5$ is (V) and Y is X;

$R_3$ is selected from H, methyl, phenyl, sulfonated phenyl, phenol, acetate, hydroxy, a fragment O—$R_1$, where $R_1$ is as defined previously, —$CO_2R_{12}$ and —$CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;

$R_8$ and $R_9$ are independently selected from hydrogen, methyl, ethyl and $C_3$-$C_4$ alkyl;

$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly ($C_2$-$C_4$ alkylene)$_b$ oxides; where b is an integer from 2 to 20;

applying the finish to at least a portion of a surface of the fiber substrate;

optionally, providing a binder material;

optionally, applying the binder material to at least a portion of the surface of the fiber substrate; and, optionally, drying the treated fiber substrate.

In another aspect of the present invention, there is provided a process for producing a treated fiber substrate comprising:

providing a fiber substrate;

providing a finish comprising at least one antimicrobial compound comprising silver complexed with a polymer; wherein the polymer comprises monomer residues selected from residue A, residue B, residue C and combinations thereof; with the proviso that the polymer contains no more than 99.5 wt % of monomer residues of residue B;

wherein residue A is

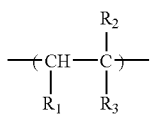

wherein residue B is

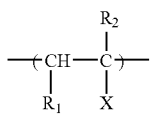

wherein residue C is

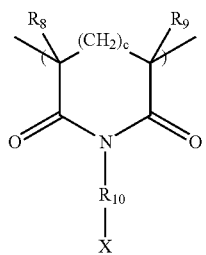

wherein
X is an unsaturated or aromatic heterocycle having at least one hetero atom selected from N, O and S;
c is 0 or 1;
$R_1$ is selected from H, $CH_3$ and —$CO_2R_4$; where $R_4$ is selected from H, $CH_3$, $C_2H_5$, a $C_3$-$C_{24}$ alkyl;
$R_2$ is selected from H, $CH_3$, $C_2H_5$, phenyl, —$CH_2CO_2R_5$ and —$CO_2R_5$; where $R_5$ is selected from (I)-(V), (I) H;

(II) 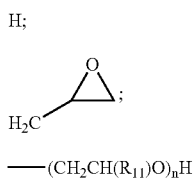

(III) —$(CH_2CH(R_{11})O)_nH$;

(IV) —$(CH_2CH(R_{11})O)_nCOCH_2COCH_3$; and, (V) 
$$\begin{array}{c} OH \\ | \\ HC-CH_2-; \\ / \\ CH_2 \\ \backslash \\ Y \end{array}$$

where $R_{11}$ is selected from H, methyl and phenyl; n is an integer from 1 to 20; Y is selected from OH, $SO_3Z$ and X; where Z is selected from H, sodium, potassium and $NH_4^+$; with the proviso that when the polymer contains 0 wt % of monomer residues of residue B and 0 wt % of monomer residues of residue C, $R_2$ is —$CH_2CO_2R_5$ or —$CO_2R_5$, $R_5$ is (V) and Y is X;

$R_3$ is selected from H, methyl, phenyl, sulfonated phenyl, phenol, acetate, hydroxy, a fragment O—$R_1$, where $R_1$ is as defined previously, —$CO_2R_{12}$ and —$CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;

$R_8$ and $R_9$ are independently selected from hydrogen, methyl, ethyl and $C_3$-$C_4$ alkyl;

$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly ($C_2$-$C_4$ alkylene)$_b$ oxides; where b is an integer from 2 to 20;

applying the finish to at least a portion of a surface of the fiber substrate;

optionally, providing a binder material;

optionally, applying the binder material to at least a portion of the surface of the fiber substrate; and, optionally, drying the treated fiber substrate.

The term "fiber" or "textile fiber" as used herein and in the appended claims refers to a unit of matter which is capable of being spun into a yarn or made into a fabric by bonding or by interlacing in a variety of ways including, for example, weaving, knitting, braiding, felting, twisting or webbing.

The term "yarn" as used herein and in the appended claims refers to a strand of textile fiber in a form suitable for weaving, knitting, braiding, felting, twisting, webbing or otherwise fabricating into a fabric.

The term "fabric" as used herein and in the appended claims refers to any material woven, non-woven, knitted, felted or otherwise produced from, or in combination with, any natural or manufactured fiber, yarn or substitute therefore.

The term "fiber substrate" as used herein and in the appended claims encompasses any fiber, textile fiber, yarn, fabric or combination thereof.

The term "treated fiber substrate" as used herein and in the appended claims refers to a fiber substrate treated with a finish of the present invention.

The term "alkyl" as used herein and in the appended claims includes both straight chain, branched and cyclic alkyl groups.

The term "alkenyl" as used herein and in the appended claims includes both straight chain and branched chain alkenyl groups.

The term "(meth)acrylates" used herein and in the appended claims encompasses both methacrylates and acrylates.

Unsaturated or aromatic heterocycles suitable for use with the present invention include, for example, 5 to 7-membered heterocycles having some degree of unsaturation; aromatic heterocycles having at least one hetero atom selected from N, O and S atoms; isomers of such heterocycles and combinations thereof. In addition, suitable heterocycles may include, for example, 5 to 7-membered heterocycles that are fused together to form larger 9 to 14 membered heterocycles having at least one N, O or S atom; isomers of such heterocycles and combinations thereof. Additional heterocycles suitable for use with the present invention include 5 to 7-membered heterocycles that are used with a carbocycle to form larger 9 to 14-membered heterocycles.

In some embodiments, the antimicrobial compositions of the present invention include a polymer comprising a heterocyclic group selected from imidazole; thiophene; pyrrole; oxazole; thiazoles and their respective isomers (e.g., thiazol-4-yl, thiazol-3-yl and thiazol-2-yl); tetrazole; pyridine;

pyridazine; pyrimidine; pyrazine; azoles; indazoles; triazoles and their respective isomers (e.g., 1,2,3-triazole and 1,2,4-triazole); and combinations thereof, such as imidazole 1,2,3-triazole-1,2,4-triazole; benzotriazole; methyl-benzotriazole; benzothiazole; methylbenzothiazole; benzimidazole and methyl benzimidazole. In some aspects of these embodiments, the antimicrobial compositions comprise a heterocycle group selected from imidazole, benzotriazole and benzimidazole. In some aspects of these embodiments, the antimicrobial compositions comprise imidazole.

In some embodiments of the present invention, the antimicrobial compositions comprise a polymer which comprises at least one heterocyclic containing monomer and at least one non-heterocyclic containing monomer. In some aspects of these embodiments, the ratio of the heterocyclic containing monomers to the non-heterocyclic containing monomers is 95:5 to 5:95; alternatively 80:20 to 20:80; alternatively 60:40 to 40:60. In some aspects of these embodiments, the at least one heterocyclic containing monomer is vinylimidazole.

In some embodiments of the present invention, the antimicrobial compositions comprise a polymer which comprises a heterocyclic containing monomer complexed with silver. In some aspects of these embodiments, the weight ratio of the heterocyclic containing monomer to silver is 95:5 to 5:95; alternatively 90:10 to 10:90; alternatively 80:20 to 20:80. In some aspects of these embodiments, the molar ratio of the silver to the heterocyclic containing monomer is 10:1 to 1:10; alternatively 4:1 to 1:4; alternatively 2:1 to 1:2. In some aspects of these embodiments, the heterocyclic containing monomer is vinylimidazole.

In some embodiments of the present invention, the antimicrobial compositions comprise a polymer which may optionally contain a crosslinking material. In some aspects of these embodiments, the polymer may contain 0.5 to 60 wt % crosslinker, alternatively at least 2 wt % crosslinker, alternatively at least 5 wt % crosslinker, alternatively at least 8 wt % crosslinker, alternatively at least 10 wt % crosslinker, alternatively at least 20 wt % crosslinker; alternatively at least 30 wt % crosslinker, alternatively at least 40 wt % crosslinker; alternatively at least 50 wt % crosslinker.

Crosslinkers suitable for use with the present invention include any known crosslinking material provided that the physical and chemical stability of the antimicrobial composition is substantially unaffected by inclusion of the crosslinking material. In some embodiments of the present invention, the antimicrobial compositions may comprise a polymer containing a multifunctional (meth)acrylate crosslinker selected from allyl methacrylate (ALMA); divinylbenzene (DVB); ethyleneglycol diacrylate (EGDA); ethyleneglycol dimethacrylate (EGDMA); 1,3-butanediol dimethacrylate (BGDMA); diethyleneglycol dimethacrylate (DEGDMA); tripropyleneglycol diacrylate (TRPGDA); trimethylolpropane trimethacrylate (TMPTMA); trimethylolpropane triacrylate (TMPTA) and combinations thereof. In some aspects of these embodiments, the antimicrobial compositions may comprise a polymer containing a crosslinker selected from TMPTMA, TMPTA and combinations thereof. In some aspects of these embodiments, the antimicrobial compositions may comprise a TMPTA crosslinker.

In some embodiments of the present invention, the antimicrobial composition may exhibit an average particle size of less than 200 nm; alternatively less than 150 nm; alternatively less than 100 nm; alternatively less than 75 nm; alternatively less than 50 nm; alternatively less than 25 nm; alternatively less than 20 nm; alternatively less than 15 nm; alternatively of 1 to 10 nm; alternatively less than 10 nm; alternatively of 1 to 8 nm; alternatively of less than 5 nm.

In some embodiments of the present invention, the antimicrobial composition comprises a polymer exhibiting a number average molecular weight of less than 500,000; alternatively of less than 100,000; alternatively of less than 50,000; alternatively less than 10,000; alternatively 1,000 to 10,000; alternatively 500 to 5,000.

In some embodiments of the present invention, the antimicrobial composition comprises a metal complexed with the polymer, wherein the metal may be selected from copper, silver, gold, tin, zinc and combinations thereof. In some aspects of these embodiments, the metal is selected from copper, silver, gold and combinations thereof. In some aspects of these embodiments, the metal is a combination of copper, silver and combinations thereof. In some aspects of these embodiments, the metal is a combination of zinc and silver. In some aspects of these embodiments, the metal is silver.

In some embodiments of the present invention, the antimicrobial composition contains 0.5 to 60 wt % metal; alternatively 0.5 to 15 wt % metal; alternatively 20 to 100,000 ppm metal; alternatively at least 20 ppm metal; alternatively 20 to 4,000 ppm metal; alternatively 20 to 1,500 ppm metal; alternatively 30 to 75 ppm metal; alternatively at least 50 ppm metal.

In some embodiments of the present invention, the antimicrobial composition contains 0.5 to 60 wt % silver; alternatively 0.5 to 15 wt % silver; alternatively 20 to 100,000 ppm silver; alternatively at least 20 ppm silver; alternatively 20 to 4,000 ppm silver; alternatively 20 to 1,500 ppm silver; alternatively 30 to 75 ppm silver; alternatively at least 50 ppm silver.

In some embodiments of the present invention, the antimicrobial composition comprises a combination of zinc and silver. In some aspects of these embodiments, the antimicrobial composition comprises 0.3 wt % to 40 wt % silver and 1 wt % to 15 wt % zinc.

In some embodiments of the present invention, the antimicrobial composition comprises a vinylimidazole copolymer complexed with silver.

As used herein and in the appended claims, the term "silver" refers to silver metal that is incorporated into an antimicrobial composition of the present invention. While not wanting to be bound as to the oxidation state of the silver ($Ag^0$, $Ag^{1+}$ or $Ag^{2+}$) that is incorporated into the antimicrobial composition, silver may be added to the antimicrobial composition by washing the polymer in a silver solution such as silver nitrate in deionized water ("DI"). Aside from DI, other liquid media can also be used such as water, aqueous buffered solutions and organic solutions such as polyethers or alcohols. Other sources of silver include but are not limited to silver acetate, silver citrate, silver iodide, silver lactate, silver picrate and silver sulfate. The concentration of silver in these solutions can vary from the concentration required to add a known quantity of silver to the antimicrobial composition to a saturated silver solution.

In some embodiments of the present invention, the finish comprises an antimicrobial composition that exhibits an inherent affinity for the surface of the fiber substrate. In some aspects of these embodiments, the finish adheres to the surface of the fiber substrate, providing the fiber substrate with a wash durable antimicrobial finish without the addition of a binder material.

In some embodiments of the present invention, the finish may further comprise an optional binder material which is applied to the fiber substrate concurrently with the antimicrobial composition.

In some embodiments of the present invention, an optional binder material may be applied to at least a portion of the surface of the fiber substrate subsequent to application of the finish.

In some embodiments of the present invention, an optional binder material may be applied to at least a portion of the surface of the fiber substrate before application of the finish.

Suitable binder materials may include any conventional binder, provided that the physical and chemical stability of the antimicrobial composition is substantially unaffected by such inclusion. In some aspects of these embodiments, the binder material may comprise a polyurethane binder, an acrylic binder, a polyvinyl acetate binder, an ethylene vinyl acetate binder, an ethylene vinyl chloride binder, a styrene butadiene rubber binder, a nitrile binder, a silicone binder, a polyvinyl alcohol binder, a phenolic binder, a thermoset binder, a polyvinyl chloride binder, a phenol formaldehyde binder, a melamine formaldehyde binder, an urea formaldehyde binder, a melamine urea binder, an isocyanate binder, an isocyanurate binder and combinations thereof. In some aspects of these embodiments, the binder material may comprise a crosslinked binder containing a crosslinking agent selected from a methylol-acrylamide, an urea, a blocked isocyanate, an epoxy, a melamine-formaldehyde, an alkoxyalkylmelamine, a carbodiimide and combinations thereof. In some aspects of these embodiments, the binder material may comprise one or more acrylic binders. In some aspects of these embodiments, the mass ratio of the binder material to the at least one antimicrobial composition may be 0:100 to 99.5:0.5; alternatively 50:50 to 99.5:0.5; alternatively 75:25 to 99.5:0.5; alternatively 80:20 to 99.5 to 0.5; alternatively 90:10 to 99.5:0.5. In some aspects of these embodiments, the binder material and the antimicrobial composition may be combined before they are applied to the surface of the fiber substrate. In some aspects of these embodiments, the binder material may be applied to the surface of the fiber substrate before the antimicrobial composition is applied to the surface of the fiber substrate. In some aspects of these embodiments, the antimicrobial composition is applied to the surface of the fiber substrate first and then the binder material is applied to the surface of the fiber substrate over top of the previously applied antimicrobial composition.

In some embodiments of the present invention, the finish may optionally further comprise an antimicrobial agent. Suitable antimicrobial agents may include any conventional antimicrobial agent provided that the physical and chemical stability of the antimicrobial composition is substantially unaffected by such inclusion. In some aspects of these embodiments, the antimicrobial agent may be selected from 3-isothiazolone; 3-iodo-2-propynylbutylcarbamate; 2-bromo-2-nitropropanediol; glutaric dialdehyde; 2-n-octyl-3-isothiazolone; sodium 2-pyridinethiol-1-oxide; p-hydroxy benzoic acid alkyl ester; tris(hydroxymethyl)nitromethane; dimethylol-dimethyl-hydantion; benzisothiazolone and 2,4,4'-trichloro-2'-hydroxy-diphenyl ether.

In some embodiments of the present invention, the finish may optionally further comprise a disinfecting agent. Suitable disinfecting agents include any conventional disinfectant, provided that the physical and chemical stability of the antimicrobial composition is substantially unaffected by such inclusion. In some aspects of these embodiments, the disinfecting agent may be selected from quaternary ammonium disinfectants, phenolic disinfectants, halide based disinfectants and combinations thereof. In some aspects of these embodiments, the disinfecting agent may be selected from a chlorine based disinfectant and a bromine based disinfectant. In some aspects of these embodiments, the disinfecting agent may be selected from an N-halamine, a bleach, a hydantoin and combinations thereof.

In some embodiments of the present invention, the treated fiber substrate may exhibit an initial applied metal concentration of 10 ppm to 500 ppm; alternatively 10 ppm to 400 ppm; alternatively 10 ppm to 300 ppm; alternatively 10 ppm to 250 ppm; alternatively 10 ppm to 200 ppm; alternatively 10 ppm to 100 ppm; alternatively less than 100 ppm; alternatively 10 ppm to 50 ppm; alternatively at least 10 ppm; alternatively at least 20 ppm; alternatively at least 30 ppm; alternatively at least 75 ppm; alternatively at least 100 ppm; alternatively at least 150 ppm; alternatively at least 200 ppm; alternatively at least 250 ppm; alternatively at least 300 ppm.

In some embodiments of the present invention, the treated fiber substrate may exhibit an initial applied silver concentration of 10 ppm to 500 ppm; alternatively 10 ppm to 400 ppm; alternatively 10 ppm to 300 ppm; alternatively 10 ppm to 250 ppm; alternatively 10 ppm to 200 ppm; alternatively 10 ppm to 100 ppm; alternatively less than 100 ppm; alternatively 10 ppm to 50 ppm; alternatively at least 10 ppm; alternatively at least 20 ppm; alternatively at least 30 ppm; alternatively at least 75 ppm; alternatively at least 100 ppm; alternatively at least 150 ppm; alternatively at least 200 ppm; alternatively at least 250 ppm; alternatively at least 300 ppm.

In some embodiments of the present invention, the treated fiber substrate is wash durable. In some aspects of these embodiments, the treated fiber substrate retains at least 50 wt % of the initial applied metal concentration after being subjected to 3 washes, wherein the washes are performed in accordance with the wash procedure set forth in AATCC Test Method 124-2001. In some aspects of these embodiments, the treated fiber substrate retains at least 50 wt %; alternatively at least 75 wt %; alternatively at least 80 wt %; alternatively at least 85 wt %; alternatively at least 90 wt %; alternatively at least 95 wt %; alternatively at least 97 wt % of the initial applied metal concentration after being subjected to at least 3 washers; alternatively at least 5 washes; alternatively at least 10 washes; alternatively at least 15 washes; alternatively at least 20 washes; alternatively after being subjected to at least 3 dry cleaning cycles, wherein the dry cleaning cycles are performed in accordance with the dry cleaning procedure set forth in AATCC Test Method 158-2000.

In some embodiments of the present invention, the treated fiber substrate is wash durable and exhibits a silver containing finish. In some aspects of these embodiments, the wash durable fiber substrate retains at least 50 wt % of the initial applied silver concentration after being subjected to 3 washes, wherein the washes are performed in accordance with the wash procedure set forth in AATCC Test Method 124-2001. In some aspects of these embodiments, the treated fiber substrate retains at least 50 wt %; alternatively at least at least 75 wt %; alternatively at least 80 wt %; alternatively at least 85 wt %; alternatively at least 90 wt %; alternatively at least 95 wt %; alternatively at least 97 wt % of the initial applied silver concentration after at least 3 washers; alternatively at least 5 washes; alternatively at least 10 washes; alternatively at least 15 washes; alternatively at least 20 washes; alternatively after being subjected to at least 3 dry cleaning cycles, wherein the dry cleaning cycles are performed in accordance with the dry cleaning procedure set forth in AATCC Test Method 158-2000.

In some embodiments of the present invention, the fiber substrate may optionally further comprise a coating, a printing, a colorant (e.g., poly(oxyalkylenated) colorants, as well as pigments, dyes and tints), an antistatic agent, a brightening compound, a nucleating agent, an antioxidant, an UV stabilizer, a filler, a permanent press finish, a softener, a lubricant, a curing accelerator, an anti-pilling agent, a reflective coating, an opacifier, a flame retardant, an anti-blocking agent and combinations thereof. In some aspects of these embodiments, the fiber substrate may optionally further comprise a soil release agent which improves wettability and washability of the fiber substrate. In some aspects of these embodiments, the fiber substrate may optionally further comprise water proofing materials including, for example, water repellent fluorocarbons and their derivatives, silicones, waxes and combinations thereof.

Fiber substrates suitable for use with the present invention include, for example, fibers, yarns, fabrics, films, foams, alginates, hydrogels and hydrocolloids. In some embodiments of the present invention, the fiber substrate may be selected from fibers, yarns, fabrics and films. In some embodiments of the present invention, the fiber substrate may be selected from fibers, yarns and fabrics.

Fibers suitable for use with the present invention include, for example, natural fibers, synthetic fibers, inorganic fibers, combinations and blends thereof. The fibers may be of any denier; may be multi- or mono-filaments; may be false twisted or twisted; may incorporate multiple denier filaments into a single yarn through twisting and/or melting; may be multicomponent fibers exhibiting any type of cross-section, including, for example, sheath/core configurations, side by side configurations, pie wedge configurations, segmented ribon configurations, segmented cross configurations, tipped trilobal configurations and conjugate configurations.

Natural fibers suitable for use with the present invention may include, for example, silk, cotton, wool, flax, fur, hair, cellulose, ramie, hemp, linen, wood pulp and combinations thereof.

Synthetic fibers suitable for use with the present invention may be derived from materials including, for example polyolefins, such as polyethylene, polypropylene and polybutylene; halogenated polymers, such as polyvinyl chloride; polyaramids, such as poly-p-phenyleneteraphthalamid (e.g. Kevlar® fibers available from DuPont), poly-m-phenyleneteraphthalamid (e.g., Nomex® fibers available from DuPont); melamine and melamine derivatives (e.g., Basofil® fibers available from Basofil Fibers, LLC); polyesters, such as polyethylene terephthalate, polyester/polyethers; polyamides, such as nylon 6 and nylon 6,6; polyurethanes, such as Tecophilic® aliphatic thermoplastic polyurethanes available from Noveon; acetates; rayon acrylics; and combinations thereof.

Inorganic fibers suitable for use with the present invention may include, for example, fiberglass, boron fibers and rock wool.

In some embodiments of the present invention, the fiber substrate may comprise one or more of Nylon-6; Nylon-6,6; polypropylene and polyethylene terephthalate.

In some embodiments of the present invention, the fiber substrate may comprise a multiplicity of fibers of any composition and of any construction. For example, in some embodiments of the present invention, the fiber substrate may comprise a knit material, a woven material, a non-woven material or a combination thereof. In some aspects of these embodiments, the fiber substrate may comprise a non-woven material.

The finish may be applied to at least a portion of the surface of a fiber substrate using any suitable method. In some embodiments of the present invention, the finish may be applied to the fiber substrate using a method selected from exhaustion, pad coating, screen coating, spray coating, roll coating, knife coating, foam coating, dip coating and combinations thereof. In some aspects of these embodiments, the finish may be applied to the fiber substrate using a method selected from pad coating, spray coating, knife coating, roll coating and combinations thereof.

In some embodiments of the present invention, the antimicrobial composition may be incorporated into a carrier medium to facilitate its application to a fiber substrate. Suitable carrier mediums may include liquids, solids, gases and combinations thereof. In some embodiments of the present invention, the antimicrobial composition may be incorporated into water as a carrier medium. In some embodiments of the present invention, the antimicrobial composition may be incorporated into a low molecular weight organic solvent as a carrier medium. In some aspects of these embodiments, the low molecular weight organic solvent may include, for example, ethanol, methanol, n-propanol, isopropanol and mixtures thereof. In some embodiments of the present invention, the antimicrobial composition may be incorporated into a mixture of one or more low molecular weight organic solvents and water as the carrier medium.

In some embodiments of the present invention, the antimicrobial composition may be applied to the fiber substrate in a dry form. In some aspects of these embodiments, the antimicrobial composition may be applied to the fiber substrate as a dry powder, a granule, a tablet, an encapsulated complex or a combination thereof.

In some embodiments of the present invention, the fiber substrate may optionally be dried subsequent to the application of the finish thereto. Optional drying of the treated fiber substrate may serve to remove moisture and other volatile components therefrom. In some aspects of these embodiments, the treated fiber substrate may be dried using a technique selected from, for example, convection drying, contact drying, radiation drying and combinations thereof.

In some embodiments of the present invention, the finish contains silver and is light stable. In some aspects of these embodiments, upon prolonged exposure of the treated fiber substrate to light in the visible spectrum, the individual values of Hunter L, a, b and L*a*b* (CIELAB) for the treated fiber substrate exhibit a change from such exposure of less than a factor of 3; alternatively of less than a factor of 2. For a description of the Hunter Color test methods, see Billmeyer, Jr. et al., PRINCIPLES OF COLOR TECHNOLOGY, John Wiley & Sons, $2^{ED}$ (1981).

The term "prolonged exposure" as used herein and in the appended claims means an intermittent exposure period of at least 24 hours; alternatively an intermittent exposure period of at least one week; alternatively an intermittent exposure period of at least one year; alternatively an intermittent exposure period of at least two years; alternatively an intermittent exposure period of at least five years. The term "intermittent exposure period" as used herein and in the appended claims refers to a period during which the exposure to light in the visible spectrum is not constant. An example of an intermittent exposure period of 24 hours would be an ambient, outdoor light cycle from dawn to dawn.

In some embodiments of the present invention, the finish contains silver and is heat stable. In some aspects of these embodiments, upon exposure of the treated fiber substrate to a temperature of at least 120° C., alternatively at least 150° C., alternatively at least 200° C., alternatively at least 300° C. for a period of at least three minutes, the individual values of Hunter L, a, b and L*a*b* (CIELAB) for the treated fiber substrate exhibit a change from such exposure of less than a factor of 3; alternatively of less than a factor of 2.

In some embodiments of the present invention, the treated fiber substrates inhibit microbial production after a 24 hour exposure at least 25%; alternatively, the treated fiber substrates exhibit at least a 1-log reduction ($\geq$90% inhibition) of microbial colony forming units per mL; alternatively at least a 2-log reduction ($\geq$99% inhibition); alternatively at least a 6-log reduction ($\geq$99.9% inhibition) of microbial colony forming units per mL. Such microbes may include, for example, *Aureobasidium pullulans, Bacillus cereus, Bacillus thuringiensis, Chaetomium globosum, Enterobacter aerogines, Escherichia coli, Gliocladtum virens, Klebsiella Pheumoniae, Legionella pneumpophila, Listeria Monocytogenes, Mycobacterium tuberculosis, Porphyromonas gingivalis, Proteus mirabilis, Proteus vulgaris, Pseudomonas aeruginosa, Saccharomyces cerevisiae, Salmonella gallinarum, Salmonella typhimurium, Staphylococcus aureus, Staphylococcus epidermidis, Streptococcus agalactiae, Streptococcus faecalis, Streptococcus mutans, Trycophyton malmsten, Vibrio parahaemolyticus, Stachybotrys, Aspergillus niger, Candida albicans* and *Penicillium funiculosum*.

In some embodiments of the present invention, the treated fiber substrates may exhibit a log kill rate for *Staphylococcus aureus* and/or *Klebsiella pneumoniae* of at least 1.5; alternatively of at least 2.0; alternatively of at least 3.0; alternatively of at least 4.0; alternatively of at least 5.0; alternatively of at least 6.0 as determined in accordance with the procedure set forth in AATCC Test Method 100-1993 for 24 hour exposure. In some aspects of these embodiments, the treated fiber substrate may exhibit a log kill rate for *Staphylococcus aureus* and/or *Klebsiella pneumoniae* of at least 1.5; alternatively of at least 2.0; alternatively of at least 3.0; alternatively of at least 4.0; alternatively of at least 5.0; alternatively of at least 6.0; wherein the log kill rate is measured after the treated fiber substrate is subjected to 3 washes; alternatively at least 3 washes; alternatively at least 5 washes; alternatively at least 10 washes; alternatively at least 15 washes; alternatively at least 20 washes performed in accordance with the wash procedure set forth in AATCC Test Method 124-2001; alternatively at least 3 dry cleaning cycles performed in accordance with the dry cleaning procedure set forth in AATCC Test Method 158-2000.

In some embodiments of the present invention, the treated fiber substrate exhibits a zone of inhibition to the growth of *Staphylococcus aureus* and/or *Klebsiella pneumoniae* as determined using a parallel streak method in accordance with AATCC Test Method 147-1988. In some aspects of these embodiments, the treated fiber substrate may continue to exhibit a zone of inhibition to the growth of *Staphylococcus aureus* and/or *Klebsiella pneumoniae* as determined using a parallel streak method in accordance with AATCC Test Method 147-1988 after the treated fiber substrate is subjected to 3 washes; alternatively at least 3 washes; alternatively at least 5 washes; alternatively at least 10 washes; alternatively at least 15 washes; alternatively at least 20 washes performed in accordance with the wash procedure set forth in AATCC Test Method 124-2001; alternatively at least 3 dry cleaning cycles performed in accordance with the dry cleaning procedure set forth in AATCC Test Method 158-2000.

In some embodiments of the present invention, the finish is non-electrically conductive. In some aspects of these embodiments, the fiber substrate is a fabric that exhibits a resistance to the flow of an electrical current of at least 10,000 ohms; alternatively of at least 1,000,000 ohms; alternatively of at least $1\times10^9$ ohms as measured using the procedure set forth in AATCC Test Method 76-1978.

The treated fiber substrates of the present invention may advantageously be used in a variety of materials to impart antimicrobial properties thereto, including, for example, apparel, apparel interlining, upholstery, carpeting, padding, ceiling tiles, acoustical tiles, backing, wall coverings, roofing products, house wraps, insulation, bedding, wiping cloths, towels, gloves, rugs, floor mats, drapery, napery, textile bags, awnings, vehicle covers, boat covers, tents, agricultural coverings, geotextiles, automotive headliners, filtration media, dust masks, fiber fill, envelopes, tags, labels, diapers, feminine hygiene products (e.g., sanitary napkins, tampons), laundry aids (e.g., fabric dryer-sheets), wound care products and medical care products (e.g., sterile wraps, caps, gowns, masks, drapings).

Some embodiments of the present invention will now be described in detail in the following Examples.

EXAMPLES 1-5

Preparation of Polymer Product

Polymer products were prepared using the following process: (a) isopropanol (515 g of 99 wt %) was charged to a one liter kettle equipped with a stirrer, dropping funnel and a condenser; (b) the contents of the kettle where heated to 80° C. with constant gentle agitation; (c) for each of Examples 1-5, a mixture with the composition set forth in Table I was slowly added to the kettle dropwise over a two hour period, while maintaining the temperature of the kettle contents at 80° C. with constant gentle agitation; (d) the product of (c) was maintained at 80° C. with constant gentle agitation for a period of thirty minutes; (e) t-amyl peroxypivalate (2 g) in isopropanol (5 g of 99 wt %) was added to the product of (d); (f) the product of (e) was maintained at 80° C. with constant gentle agitation for a period of thirty minutes; (g) t-amyl peroxypivalate (2 g) in isopropanol (5 g of 99 wt %) was added to the product of (f); (h) the product of (g) was maintained at 80° C. with constant gentle agitation for a period of thirty minutes; (i) t-amyl peroxypivalate (2 g) in isopropanol (5 g of 99 wt %) was added to the product of (h); (j) the product of (i) was maintained at 80° C. with constant gentle agitation for a period of thirty minutes; (k) the heating source was removed and the product of (j) was allowed to cool to room temperature to leave the product polymer in isopropanol in Examples 2-5; and, (l) the isopropanol in Example 1 was removed from the product of (k) under vacuum to leave the polymer product.

TABLE I

| Component | Ex. 1 | Ex. 2 | Ex. 3 | Ex. 4 | Ex. 5 |
| --- | --- | --- | --- | --- | --- |
| butyl acrylate (BA) | 40 g | 40 g | 45 g | 40 g | 40 g |
| vinylimidazole (VI) | 40 g | 50 g | 45 g | 0 g | 40 g |
| 1-vinylpyrrolidone | 0 g | 0 g | 0 g | 40 g | 0 g |
| acrylic acid (AA) | 10 g | 0 g | 10 g | 10 g | 10 g |
| trimethylolpropane triacylate (TMPTA) | 10 g | 10 g | 0 g | 10 g | 10 g |
| t-amyl peroxypivalate | 2 g | 2 g | 2 g | 2 g | 2 g |

TABLE I-continued

| Component | Ex. 1 | Ex. 2 | Ex. 3 | Ex. 4 | Ex. 5 |
|---|---|---|---|---|---|
| isopropanol | 25 g | 25 g | 25 g | 25 g | 25 g |
| Average particle diameter of polymer product | 1.6 nm | 1.4 nm | 1.5 nm | 1.6 nm | — |

EXAMPLE 6

Preparation of Antimicrobial Composition

An antimicrobial composition comprising silver complexed with a polymer containing crosslinked imidazole was prepared as follows: (a) a uniform sample of the polymer product from Example 1 (3 g) was dispersed in deionized water (17 g); (b) ethanol (17 g of 95 wt %) was added to product of (a) with agitation; (c) an aqueous solution of silver nitrate (0.44 g $AgNO_3$ in 5 g of deionized water) was added to product of (b) with agitation, forming a white precipitate; and, (d) an aqueous ammonium hydroxide solution (4.4 g of a 5 wt % solution) was added to the product of (c) with agitation forming a product clear light yellow colored solution containing an antimicrobial composition containing 0.53 wt % silver.

EXAMPLE 7

Preparation of Control

A control was prepared as follows: (a) a uniform sample of the polymer product from Example 1 (9 g) was dispersed in deionized water (51 g); (b) ethanol (51 g of 95 wt %) was added to the product of (a) with agitation; and, (c) an aqueous ammonium hydroxide solution (12.3 g of a 5 wt % solution) was added to the product of (b) with agitation forming the control finish.

EXAMPLE 8

Preparation of Antimicrobial Composition

An antimicrobial composition comprising silver complexed with an imidazole containing polymer was prepared as follows: (a) a uniform sample of the polymer product from Example 3 (15 g of polymer solids in 85 g isopropanol) was mixed with deionized water (85 g) and an aqueous ammonium hydroxide solution (15 g of a 10 wt % solution); (b) an aqueous silver nitrate solution (2.2 g $AgNO_3$ in 10 g or deionized water) was added to the product of (a) with agitation, forming a hazy light yellow colored solution; and, (c) the product of (b) was filtered, leaving a product clear light yellow filtrate containing 0.62 wt % silver.

EXAMPLE 9

Preparation of Antimicrobial Composition

An antimicrobial composition comprising silver complexed with a pyrrolidone containing polymer was prepared as follows: (a) a uniform sample of the polymer product from Example 4 (16.5 g of polymer solids in 83.5 g isopropanol) was mixed with deionized water (6.2 g); (b) isopropanol (6 g) and an aqueous ammonium hydroxide solution (15 g of 10 wt % solution) was added to the product of (a) with agitation; and, (c) an aqueous silver nitrate solution (2.2 g $AgNO_3$ in 10 g deionized water) was added to the product of (b) with agitation, forming a product colorless clear solution containing 0.63 wt % silver.

EXAMPLE 10

Preparation of Antimicrobial Composition (Without Ammonia)

An antimicrobial composition comprising silver complexed with a crosslinked imidazole containing polymer was prepared as follows: (a) a uniform sample of the polymer product from Example 1 (3.7 g) was dispersed in deionized water (6.2 g); (b) isopropanol (6 g of 99 wt %) and 2-amino-2-methylpropanol (1.5 g) were added to the product of (a) with agitation; and, (c) an aqueous silver nitrate solution (0.7 g $AgNO_3$ in 2 g of deionized water) was added to product of (b) with agitation, forming a product light yellow solution containing 2.2 wt % silver.

EXAMPLE 11

Preparation of Antimicrobial Composition

An antimicrobial composition comprising silver complexed with a crosslinked imidazole containing polymer was prepared as follows: (a) a uniform sample of the polymer product from Example 1 (3 g) was dispersed in deionized water (17 g); (b) ethanol (20 g of 95 wt %) was added to the product of (a) with agitation; (c) an aqueous silver nitrate solution (0.2 g $AgNO_3$ in 2 g of deionized water) was added to the product of (b) with agitation, forming a gummy white precipitate; and, (d) an aqueous ammonium hydroxide solution (1.7 g of a 14 wt % solution) was added to the product of (c) with agitation, forming a product clear light yellow colored solution containing 0.31 wt % silver.

EXAMPLE 12

Preparation of Antimicrobial Composition

An antimicrobial composition comprising silver complexed with a crosslinked imidazole and polyvinylpyrrolidone containing polymer was prepared as follows: (a) a uniform sample of the polymer product from Example 1 (3 g) was dispersed in deionized water (17 g); (b) ethanol (20 g of 95 wt %) was added to the product of (a) with agitation; (c) an aqueous silver nitrate solution (0.2 g $AgNO_3$ in 2 g of deionized water) was added to the product of (b) with agitation, forming a white precipitate; and, (d) polyvinylpyrrolidone (0.4 g) was added to the product of (c) with agitation, forming a product clear light yellow colored solution containing 0.32 wt % silver.

EXAMPLE 13

Preparation of Antimicrobial Composition

An antimicrobial composition comprising silver complexed with a crosslinked imidazole containing polymer was prepared as follows: (a) a uniform sample of the polymer product from Example 5 (1.5 g polymer solids in 8.5 g isopropanol) was dispersed in deionized water (0.5 g); (b) isopropanol (3.0 g of 99 wt %) was added to product of (a) with agitation; (c) an aqueous solution of silver nitrate (0.6 g $AgNO_3$ in 5 g of deionized water) was added to product of (b) with agitation, forming a white precipitate; and, (d) an aqueous ammonium hydroxide solution (2.0 g of a 28 wt % solution) was added to the product of (c) with agitation forming a product clear light yellow colored solution containing 2.09 wt % silver.

EXAMPLE 14

Preparation of Antimicrobial Composition

An antimicrobial composition comprising silver complexed with a crosslinked imidazole containing polymer was prepared as follows: (a) a uniform sample of the polymer product from Example 5 (15 g polymer solids in 85 g isopropanol) was dispersed in deionized water (85 g); (b) an aqueous ammonium hydroxide solution (15 g of a 10 wt % solution) was added to the product of (a) with agitation; and, (c) a solution of silver nitrate (2.2 g $AgNO_3$ in 10 ml of deionized water) was added to product of (b) with agitation, forming a yellow solution containing 0.65 wt % Ag.

EXAMPLES 15-24

Preparation of Finishes Comprising Antimicrobial Compositions

Finishes comprising an antimicrobial composition comprising silver complexed with a polymer were prepared using the following procedure with the respective quantities listed in Table II: (a) an acrylic polymer containing latex emulsion was mixed with deionized water; and, (b) a uniform sample of the product solution from one of Examples 6, 8, 13 or 14 was added to the product of (a) with agitation, forming a product formulation containing the concentration of silver indicated in Table II.

EXAMPLES 25-27

Preparation of Controls

Controls were prepared using the following procedure with the respective quantities listed in Table III: (a) an acrylic polymer containing latex emulsion was mixed with deionized water.

TABLE III

| Component | Example 25 | Example 26 | Example 27 |
|---|---|---|---|
| latex emulsion I[¥] | 113.6 g | 0 g | 0 g |
| latex emulsion II[¶] | 0 g | 108.7 g | 0 g |
| latex emulsion III[F] | 0 g | 0 g | 100 g |
| Distilled water | 867.2 g | 891.3 g | 900 g |
| Silver concentration | 0 ppm | 0 ppm | 0 ppm |

[¥]Acrylic polymer containing latex commercially available from Rohm and Haas Company of Philadelphia, Pennsylvania as Rhoplex ™ NW-1845K.
[¶]Acrylic polymer containing latex commercially available from Rohm and Haas Company of Philadelphia, Pennsylvania as Rhoplex ™ B-15J.
[F]Acrylic polymer containing latex commercially available from Rohm and Haas Company of Philadelphia, Pennsylvania as Rhoplex ™ TR-25.

EXAMPLE 28

Preparation of Control

A control was prepared using the following procedure: (a) deionized water (867.2 g) was mixed with an acrylic polymer containing latex emulsion (113.6 g of Rhoplex™NW-1845K from Rohm and Haas Company of Philadelphia, Pa.); and, (b) a uniform sample of polymer product solution from Example 7 (19.2 g) was added to the product of (a) with agitation, forming a control finish containing 0 ppm of silver.

TABLE II

| Component | Ex. 15 | Ex. 16 | Ex. 17 | Ex. 18 | Ex. 19 |
|---|---|---|---|---|---|
| latex emulsion I[¥] | 113.6 g | 113.6 g | 0 g | 0 g | 0 g |
| latex emulsion II[¶] | 0 g | 0 g | 108.7 g | 108.7 g | 54.4 g |
| latex emulsion III[F] | 0 g | 0 g | 0 g | 0 g | 0 g |
| Product of Ex. 6 | 6 g | 12 g | 6 g | 12 g | 0 g |
| Product of Ex. 8 | 0 g | 0 g | 0 g | 0 g | 0 g |
| Product of Ex. 13 | 0 g | 0 g | 0 g | 0 g | 0 g |
| Product of Ex. 14 | 0 g | 0 g | 0 g | 0 g | 6 g |
| Distilled water | 880.4 g | 874.4 g | 885.3 g | 879.3 g | 439.6 g |
| Silver concentration as ($Ag^+$) | 27 ppm | 57 ppm | 37 ppm | 79 ppm | 77 ppm |

| Component | Ex. 20 | Ex. 21 | Ex. 22 | Ex. 23 | Ex. 24 |
|---|---|---|---|---|---|
| latex emulsion I[¥] | 0 g | 0 g | 0 g | 0 g | 0 g |
| latex emulsion II[¶] | 54.4 g | 0 g | 0 g | 54.4 g | 0 g |
| latex emulsion III[F] | 0 g | 50.0 g | 50.0 g | 0 g | 50.0 g |
| Product of Ex. 6 | 0 g | 0 g | 0 g | 0 g | 0 g |
| Product of Ex. 8 | 0 g | 0 g | 0 g | 6.9 g | 6.9 g |
| Product of Ex. 13 | 2.0 g | 0 g | 2.0 g | 0 g | 0 g |
| Product of Ex. 14 | 0 g | 6 g | 0 g | 0 g | 0 g |
| Distilled water | 443.6 g | 444.0 g | 448.0 g | 438.7 g | 443.1 |
| Silver concentration as ($Ag^+$) | 86 ppm | 72 ppm | 90 ppm | 100 ppm | 100 ppm |

[¥]Acrylic polymer containing latex commercially available from Rohm and Haas Company of Philadelphia, Pennsylvania as Rhoplex ™ NW-1845K.
[¶]Acrylic polymer containing latex commercially available from Rohm and Haas Company of Philadelphia, Pennsylvania as Rhoplex ™ B-15J.
[F]Acrylic polymer containing latex commercially available from Rohm and Haas Company of Philadelphia, Pennsylvania as Rhoplex ™ TR-25.

EXAMPLE 29

PolyCotton Fabric Treated with a Control/Finish

Polycotton material used for testing was 50/50 polycotton test fabric obtained from Testfabrics, Inc. of West Pittston, Pa. The polycotton material was pretreated by first rinsing the material in hot water (~60° C.) in a home style, top loading, washing machine on a 15 minute wash cycle. The polycotton material was then dried in a home style dryer on a normal setting. The polycotton material was then pad treated with a control or a finish by passing through a solution of one of Examples 19, 20, 21, 22, 23, 24, 26 or 27. Excess solution was squeezed from the polycotton material by passing the polycotton material through a roller nip with a pressure of 2 bar. The treated polycotton material was then dried at 149° C. for 2 minutes.

EXAMPLE 30

Polyester Fabrics Treated with a Control/Finish

Weighed pieces of 1 oz/yd$^2$ pointbonded polyethylene terephthalate (PET) web were pad treated with a control or a finish by passing through a solution of one of Examples 15, 16, 17, 18, 19, 20, 21, 22, 23, 24, 25, 26 or 27. Excess solution was squeezed from the web by passing the web through a roller nip with a pressure of 2 bar. The samples were then dried at 149° C. for 2 minutes.

EXAMPLE 31

Wash Procedure

Treated samples of polycotton and polyester fabrics prepared according to Examples 29 and 30, respectively, were subjected to 0, 3 and 5 wash cycles and one drying cycle performed in accordance with the procedure set forth in AATCC Test Method 124-2001.

EXAMPLE 32

Dry Cleaning Procedure

Treated samples of polycotton fabrics prepared according to Example 29 were subjected to 3 dry cleaning cycles performed in accordance with the procedure set forth in AATCC Test Method 158-2000.

EXAMPLE 33

Silver Content Analysis of Treated Polycotton and Polyester Fabrics

The dried, treated fabric samples prepared according to Examples 29 and 30 were analyzed for silver content by the following procedure, namely: (a) an aliquot of 0.5 g of dried fabric material was weighed into a quartz beaker and covered with a Teflon® watch glass; (b) concentrated sulfuric acid (10 ml of trace metal grade) was added to (a); (c) the quartz beaker was then placed on a hot plate; (d) heat was slowly increased to char the contents of the quartz beaker; (e) the solution in the quartz beaker was then oxidized by adding nitric acid (trace metal grade) dropwise until a clear solution was produced; (f) the clear solution of (e) was allowed to cool; (g) the Teflon® watch glass and sides of the quartz beaker were rinsed and the rinse material was retained in the quartz beaker; (h) the quartz beaker and its contents were heated to evaporate the solution until approximately 1 ml remained in the quartz beaker; (i) the product of (h) was made up to 25 ml with millipore water; and (i) a sample of the product of (i) was then analyzed using a Perkin Elmer 4300 DV Spectrometer.

A series of silver calibration standards were prepared from reference materials to bracket the concentration found in the tested samples. An analytical line used for the analysis was 328.068 nm in an axial mode. The results of the silver content analyses of the tested samples are provided in Table VI.

TABLE VI

| Sample Treated with Product Solution of | Fiber Substrate Type | after 0 washes | after 3 washes | after 5 washes | after 3 dry cleaning cycles |
|---|---|---|---|---|---|
| Example 15 | PET | 100 ppm | — | — | — |
| Example 16 | PET | 180 ppm | — | — | — |
| Example 17 | PET | 90 ppm | — | — | — |
| Example 18 | PET | 180 ppm | — | — | — |
| Example 25 | PET | ND | — | — | — |
| Example 28 | PET | ND | — | — | — |
| Example 19 | PET | 212 ppm | 242 ppm | — | — |
| Example 19 | PolyCotton | 103 ppm | — | 66 ppm | 90 ppm |
| Example 20 | PET | 348 ppm | 289 ppm | — | — |
| Example 20 | PolyCotton | 128 ppm | — | 66 ppm | 110 ppm |
| Example 21 | PET | 303 ppm | 245 ppm | — | — |
| Example 21 | PolyCotton | 127 ppm | — | 59 ppm | 88 ppm |
| Example 22 | PET | 367 ppm | 250 ppm | — | — |
| Example 22 | PolyCotton | 143 | — | 66 | 67 |
| Example 23 | PET | 323 | 280 | — | — |
| Example 23 | PolyCotton | 114 | — | 66 | 85 |
| Example 24 | PET | 382 | 279 | — | — |
| Example 24 | PolyCotton | 145 | — | 68 | 69 |
| Example 26 | PET | ND | ND | — | — |
| Example 26 | PolyCotton | ND | — | ND | ND |
| Example 27 | PET | ND | ND | — | — |
| Example 27 | PolyCotton | ND | — | ND | ND |

EXAMPLE 34

Tensile Strength of Treated Polyester Fabrics

The tensile strength of 1"×5" samples of some of the treated polyester fabric prepared according to Example 30 was measured using an Instron in both the machine direction (MD) and the cross direction (CD) for each of the following conditions: dry, wet with water and wet in isopropanol. The wet samples were immersed in solvent for a period of 30 minutes and tested immediately upon removal from the solvent after passage through and Instron with a 2 inch gap setting, at a 12 in/min crosshead speed and a 10 lb or 100 lb load cell setting. The results are provided in Table VII.

TABLE VII

| | Tensile Strength (in lbs) | | | | | |
|---|---|---|---|---|---|---|
| Sample Treated with | Dry | | Water | | Isopropanol | |
| Product Solution of | MD | CD | MD | CD | MD | CD |
| Example 15 | 11.4 | 2.2 | 4.0 | 0.8 | 0.9 | 0.2 |
| Example 16 | 11.5 | 2.3 | 3.6 | 0.8 | 0.9 | 0.2 |
| Example 17 | 6.0 | 1.9 | 2.9 | 0.7 | 1.0 | 0.2 |
| Example 18 | 10.5 | 2.2 | 2.9 | 0.8 | 1.0 | 0.2 |
| Example 25 | 6.8 | 1.5 | 3.2 | 0.9 | 1.5 | 0.4 |

TABLE VII-continued

| Sample Treated with | Tensile Strength (in lbs) | | | | | |
|---|---|---|---|---|---|---|
| | Dry | | Water | | Isopropanol | |
| Product Solution of | MD | CD | MD | CD | MD | CD |
| Example 26 | 8.9 | 1.8 | 2.9 | 0.7 | 0.8 | 0.2 |
| Example 28 | 11.2 | 2.7 | 4.0 | 1.0 | 1.2 | 0.3 |

EXAMPLE 35

Color of Treated Polyester Fabric

The color of some of the treated polyester fabric prepared according to Example 30 was measured using a Minolta Chroma Meter CR-331 with bidirectional illumination from a pulsed xenon arc source, a 45 degree illumination angle and a 0 degree viewer angle with a 25 mm measuring area. The actual measurements were performed on 4 layers of the treated polyester fabric samples using a Black Lenata card as backing. The results are provided in Table VIII. Note that the values reported in Table VIII represent the average for three individual readings take at each of three different spots on the surface of the samples.

TABLE VIII

| Sample Treated with Product Solution of | L value¥ | a value† | b value† |
|---|---|---|---|
| Example 15 | 86.68 | −3.92 | +2.96 |
| Example 16 | 86.17 | −3.92 | +2.41 |
| Example 17 | 86.55 | −3.92 | +1.87 |
| Example 18 | 86.58 | −3.91 | +1.80 |
| Example 25 | 87.51 | −4.05 | +2.32 |
| Example 26 | 86.45 | −3.86 | +1.84 |
| Example 28 | 86.22 | −4.02 | +2.27 |

¥L = light/dark; range is 0-100, closer to 100 the more white.
† a = red/green; range is −∞ to +∞, the more negative the more red.
†b = yellow/blue; range is −∞ to +∞, the more negative the more blue.

EXAMPLE 36

Hand of Treated Polyester Fabric

The hand of some of the treated polyester fabric prepared according to Example 30 was measured using a Thwing-Albert Handle-O-Meter Model 211-5. A specimen size of 4"×4" was used with a 10 mm gap setting and a 1" insertion. The results are reported in Table IX. The results provided represent the average value obtained for two individual specimens of each treated polyester fabric with 4 different directional measurements.

TABLE IX

| Sample Treated with | Stiffness (gms) | |
|---|---|---|
| Product Solution of | Group I | Group II |
| Example 15 | 17.6 | 17.1 |
| Example 16 | 20.4 | 18.9 |
| Example 17 | 18.6 | 17.1 |
| Example 18 | 18.7 | 19.2 |
| Example 25 | 16.7 | 15.8 |
| Example 26 | 17.0 | 16.7 |
| Example 28 | 22.0 | 21.8 |

EXAMPLE 37

Antibacterial Activity of Treated PolyCotton and Polyester Fabrics

The antibacterial activity of the treated polycotton and polyester fabrics prepared according to Examples 29 and 30 and washed or dry cleaned according to Examples 31 and 32, respectively, was measured using a parallel streak method (AATCC Test Method 147-1988). The test samples were placed on nutrient agar inoculated with parallel streaks of the bacteria:

(a) *Staphylococcus aureus* (ATCC 6538); and (b) *Klebsiella pneumoniae* (ATCC 4352).

Following an incubation period of 24 hours at 37° C., antibacterial activity was evaluated by measuring (in mm) the size of any clear zone of no growth (Zone of Inhibition) around each sample, and visually determining growth in the contact area. The results are provided below in Table X.

In analyzing the data presented in Table X, note that No Growth Contact Area ("NGCA") designation is routinely used in bacterial tests. Bacterial organisms are often difficult to determine on a sample itself. Hence, the area immediately beneath the sample is examined for bacterial growth. A NGCA designation is indicated when there are no bacterial colonies detected immediately under the sample. Note also that a Growth Contact Area ("GCA") designation is similarly routinely used in bacterial tests. A GCA designation is indicated when there are colonies of bacterial detected immediately under the sample.

TABLE X

| | | AATCC Test Method 147-1988 | | | | | | | |
|---|---|---|---|---|---|---|---|---|---|
| Sample | | Zone of Inhibition (mm)/growth in contact area | | | | | | | |
| Treated with | Fiber | *Staphylococcus aureus* | | | | *Klebsiella pneumoniae* | | | |
| Product Solution of | Substrate Type | 0 Washes | 3 Washes | 5 Washes | 3 Dry Cleanings | 0 Washes | 3 Washes | 5 Washes | 3 Dry Cleanings |
| Example 15 | PET | 0/NGCA | — | — | — | 1/NGCA | — | — | — |
| Example 16 | PET | 0.5/NGCA | — | — | — | 2/NGCA | — | — | — |

TABLE X-continued

AATCC Test Method 147-1988

| Sample | | Zone of Inhibition (mm)/growth in contact area | | | | | | | |
|---|---|---|---|---|---|---|---|---|---|
| Treated with | Fiber | Staphylococcus aureus | | | | Klebsiella pneumoniae | | | |
| Product Solution of | Substrate Type | 0 Washes | 3 Washes | 5 Washes | 3 Dry Cleanings | 0 Washes | 3 Washes | 5 Washes | 3 Dry Cleanings |
| Example 17 | PET | 2/NGCA | — | — | — | 4/NGCA | — | — | — |
| Example 18 | PET | 4/NGCA | — | — | — | 6/NGCA | — | — | — |
| Example 25 | PET | 0/GCA | — | — | — | 0/GCA | — | — | — |
| Example 28 | PET | 0/GCA | — | — | — | 0/GCA | — | — | — |
| Example 19 | PET | 5/NGCA | 5/NGCA | — | — | 6/NGCA | 6/NGCA | — | — |
| Example 19 | PolyCotton | 5/NGCA | — | 4/NGCA | 4/NGCA | 7/NGCA | — | 1/NGCA | 5/NGCA |
| Example 20 | PET | 7/NGCA | 5/NGCA | — | — | 5/NGCA | 6/NGCA | — | — |
| Example 20 | PolyCotton | 6/NGCA | — | 4/NGCA | 4/NGCA | 7/NGCA | — | 3/NGCA | 6/NGCA |
| Example 21 | PET | 2/NGCA | 0/GCA | — | — | 3/NGCA | 0/GCA | — | — |
| Example 21 | PolyCotton | 3/NGCA | — | 1/NGCA | 3/NGCA | 5/NGCA | — | 0/NGCA | 5/NGCA |
| Example 22 | PET | 2/NGCA | 0/GCA | — | — | 1/NGCA | 0/GCA | — | — |
| Example 22 | PolyCotton | 4/NGCA | — | 0.5/NGCA | 4/NGCA | 5/NGCA | — | 0/GCA | 5/NGCA |
| Example 23 | PET | 4/NGCA | 6/NGCA | — | — | 6/NGCA | 2/NGCA | — | — |
| Example 23 | PolyCotton | 5/NGCA | — | 5/NGCA | 4/NGCA | 7/NGCA | — | 1/NGCA | 5/NGCA |
| Example 24 | PET | 0/GCA | 0/GCA | — | — | 2/NGCA | 0/GCA | — | — |
| Example 24 | PolyCotton | 3/NGCA | — | 1/NGCA | 3/NGCA | 6/NGCA | — | 0/GCA | 4/NGCA |
| Example 26 | PET | 0/GCA | 0/GCA | — | — | 0/GCA | 0/GCA | — | — |
| Example 26 | PolyCotton | 0/GCA | — | 0/GCA | 0/GCA | 0/GCA | — | 0/GCA | 0/GCA |
| Example 27 | PET | 0/GCA | 0/GCA | — | — | 0/GCA | 0/GCA | — | — |
| Example 27 | PolyCotton | 5/NGCA$ | — | 0/GCA | 0/GCA | 7/NGCA$ | — | 0/GCA | 0/GCA |

$Rhoplex™ TR-25 contains formaldehyde as an in-can preservative material. It is believed that the antimicrobial activity observed in these test samples resulted from the formaldehyde content of the Rhoplex™ TR-25.

EXAMPLE 38

Bacteriostatic Activity of Treated Polyester Fabrics

The bacteriostatic activity of some of the treated polyester fabric prepared according to Example 30 was measured using AATCC Method 100-1993. The test samples were quantitatively evaluated for bacteriostatic activity by placing 1.0 ml of a diluted culture of the test bacterial ($10^5$ organisms) in direct contact with the sterilized sample. Following a 24 hour incubation period at 37° C. and 100% relative humidity, the samples were diluted with sterile letheen broth and the number of surviving organisms were determined by the standard plate count. The percent reduction was calculated by comparison to the number of organisms recovered at zero contact time. The results of these analyses are provided in Table XI.

EXAMPLE 39

Antifungal Activity of Treated Polycotton and Polyester Fabrics

The antifungal activity of the treated polycotton and polyester fabrics prepared according to Examples 29 and 30 and washed or dry cleaned according to Examples 31 and 32, respectively, was measured using AATCC Method 30-1989. The test samples were placed on non-nutrient mineral salts agar and inoculated with a fungal spore suspension of *Aspergillus niger*. After a 14 day incubation period at 28° C., antifungal activity was evaluated by visually rating the degree of growth on the test samples using the following scale:

TABLE XI

AATCC Test Method 100-1993

| Sample | | Number of surviving organisms | | | | | |
|---|---|---|---|---|---|---|---|
| Treated with | | Staphylococcus aureus | | | Lkebsiella pneumoniae | | |
| Product Solution of | at 0 time | after 24 hrs | % reduction | at 0 time | after 24 hrs | % reduction |
| Example 15 | $2.0 \times 10^5$ | $4.0 \times 10^2$ | 99.8 | $1.6 \times 10^5$ | $3.0 \times 10^2$ | 99.8 |
| Example 16 | $2.4 \times 10^5$ | $8.0 \times 10^2$ | 99.7 | $1.3 \times 10^5$ | <100 | >99.9 |
| Example 17 | $2.9 \times 10^5$ | $5.0 \times 10^2$ | 99.8 | $1.2 \times 10^5$ | <100 | >99.9 |
| Example 18 | $3.4 \times 10^5$ | $2.3 \times 10^3$ | 99.3 | $1.4 \times 10^5$ | <100 | >99.9 |
| Example 25 | $3.1 \times 10^5$ | $1.9 \times 10^6$ | <0.01 | $1.4 \times 10^5$ | $1.2 \times 10^6$ | <0.01 |
| Example 26 | $3.4 \times 10^5$ | $1.4 \times 10^6$ | <0.01 | $1.8 \times 10^5$ | $1.6 \times 10^6$ | <0.01 |
| Example 28 | $2.6 \times 10^5$ | $1.3 \times 10^6$ | <0.01 | $1.5 \times 10^5$ | $18.1 \times 10^5$ | <0.01 |

| | |
|---|---|
| No Growth | (NG) |
| Traces of Growth (less than 10% coverage) | (TG) |
| Light Growth (10 to 30% coverage) | (LG) |
| Moderate Growth (30 to 60% coverage) | (MG) |
| Heavy Stain (at least 60% coverage) | (HG) |

The results of the tests are provided in Table XII.

TABLE XII

AATCC Test Method 30-1989

| Sample Treated with Product Solution of | Fiber Substrate Type | *Aspergillus niger* | | | |
|---|---|---|---|---|---|
| | | 0 Washes | 3 Washes | 5 Washes | 3 Dry Cleanings |
| Example 15 | PET | NG | — | — | — |
| Example 16 | PET | NG | — | — | — |
| Example 17 | PET | NG | — | — | — |
| Example 18 | PET | NG | — | — | — |
| Example 25 | PET | LG | — | — | — |
| Example 28 | PET | LG | — | — | — |
| Example 19 | PET | NG | LG | — | — |
| Example 19 | PolyCotton | NG | — | MG | HG |
| Example 20 | PET | NG | LG | — | — |
| Example 20 | PolyCotton | NG | — | MG | HG |
| Example 21 | PET | NG | MG | — | — |
| Example 21 | PolyCotton | LG | — | LG | LG |
| Example 22 | PET | NG | LG | — | — |
| Example 22 | PolyCotton | NG | — | LG | MG |
| Example 23 | PET | NG | LG | — | — |
| Example 23 | PolyCotton | NG | — | LG | MG |
| Example 24 | PET | NG | LG | — | — |
| Example 24 | PolyCotton | NG | — | MG | HG |
| Example 26 | PET | MG | MG | — | — |
| Example 26 | PolyCotton | HG | — | MG | HG |
| Example 27 | PET | MG | LG | — | — |
| Example 27 | PolyCotton | MG | — | MG | MG |

EXAMPLE 40

Preparation of Polymer Product

A polymer product was prepared using the following process: (a) Reagent grade alcohol (280 g) was fed to a one liter kettle equipped with a stirrer, a water-cooled reflux condenser with a nitrogen gas purge outlet, a thermocouple attached to an I$^2$R Tow TC Adapter Model TCA/1 temperature controller, a co-feed line controlled by a Harvard Apparatus 22 syringe drive and a monomer feed line controlled by QG-50 FMI pump fitted with ¼ inch tubing; (b) the contents of the kettle were heated to 80° C. with constant gentle agitation; (c) a monomer mixture containing 40 g lauryl acrylate, 40 g 1-vinylimidazole, 10 g acrylic acid and 10 g trimethylolpropane triacrylate in 25 g reagent grade alcohol was fed to the kettle at a constant rate over 2 hours and a solution of t-amyl peroxypivalate (Triganox® 125-C75 available from Akzo Noble Polymer Chemicals) in 30 g of reagent grade alcohol was co-fed to the kettle at a constant rate over 2 hours; (d) the product of (c) was maintained at 80° C. with constant gentle agitation for a period of thirty minutes; (e) t-amyl peroxypivalate (2 g) was fed to the kettle; (f) the product of (e) was maintained at 80° C. with constant gentle agitation for a period of thirty minutes; (g) t-amyl peroxypivalate (2 g) was fed to the kettle; (h) the product of (g) was maintained at 80° C. with constant gentle agitation for a period of thirty minutes; (i) t-amyl peroxypivalate (2 g) was fed to the kettle; (j) the product of (i) was maintained at 80° C. with constant gentle agitation for a period of thirty minutes; and, (k) the product of (j) was allowed to cool to room temperature, giving the polymer product as a polymer solution containing 21 wt % polymer solids with an average particle diameter of 7.2 nm.

EXAMPLE 41

Preparation of Antimicrobial Composition

An antimicrobial composition comprising silver complexed with a crosslinked imidazole containing polymer was prepared as follows: (a) to a uniform sample of the polymer product of Example 40 (10 g polymer solution) was added an aqueous ammonium hydroxide (2.0 g of a 28 wt % solution); and, (b) an aqueous solution of silver nitrate (0.53 g AgNO$_3$ in 0.5 g of deionized water) was added to the product of (a) with agitation forming a product clear light yellow colored solution containing 2.13 wt % silver.

EXAMPLE 42

Treatment of Rayon with a Control/Finish

Rayon web material with a target weight of 0.75-1.0 oz/yd$^2$ was bonded using a latex binder (Rhoplex® ST-954 available from Rohm and Haas Company) at 0.25 oz/yd$^2$. A finish comprising the antimicrobial composition prepared in Example 41 was applied to samples of the rayon web material by (a) passing the rayon web materials through a bath solution containing various amounts of the antimicrobial composition, (b) passing the rayon web materials through a roller nip with a pressure of 2 bar to remove excess bath solution and (c) then drying the rayon web materials for 2 minutes at 149° C. Four different bath solutions were used to treat samples of the rayon web material. The bath solutions were prepared by adding a quantity of the antimicrobial composition prepared in Example 41 to obtain the theoretical silver concentration listed in Table XIII. The pH of the bath solutions was then adjusted to 8-8.5 with an aqueous ammonium hydroxide solution. The silver concentration in the finish treated rayon web materials was then determined using Inductively Coupled Plazma analysis (ICP) and the results are presented in Table XIII.

TABLE XIII

| Theoretical Ag$^+$ in Bath Solution | Measured Ag$^+$ in finish treated rayon |
|---|---|
| 0 ppm | 1.2 ppm |
| 25 ppm | 181 ppm |
| 50 ppm | 262 ppm |
| 100 ppm | 488 ppm |

What is claimed is:

1. A treated fiber substrate having a surface, wherein at least a portion of the surface is treated with a finish, wherein the finish comprises at least one antimicrobial composition comprising a metal complexed with a polymer, wherein the metal is selected from copper, silver, gold, tin, zinc and combinations thereof; and, wherein the polymer comprises monomer residues selected from residue A, residue B, residue C and combinations thereof; with the proviso that the polymer contains no more than 99.5 wt % of monomer residues of residue B;

wherein residue A is

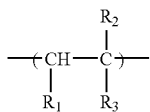

wherein residue B is

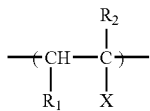

wherein residue C is

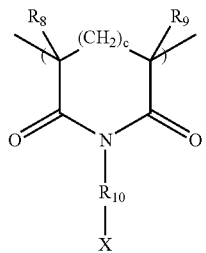

wherein
X is an unsaturated or aromatic heterocycle having at least one hetero atom selected from N, O and S;
c is 0 or 1;
$R_1$ is selected from H, $CH_3$ and —$CO_2R_4$; where $R_4$ is selected from H, $CH_3$, $C_2H_5$, a $C_3$-$C_{24}$ alkyl;
$R_2$ is selected from H, $CH_3$, $C_2H_5$, phenyl, —$CH_2CO_2R_5$ and —$CO_2R_5$; where $R_5$ is selected from (I)-(V),

H;   (I)

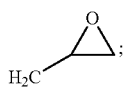   (II)

—$(CH_2CH(R_{11})O)_nH$;   (III)

—$(CH_2CH(R_{11})O)_nCOCH_2COCH_3$; and,   (IV)

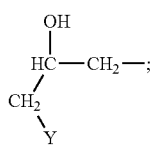   (V)

where $R_{11}$ is selected from H, methyl and phenyl; n is an integer from 1 to 20; Y is selected from OH, $SO_3Z$ and X; where Z is selected from H, sodium, potassium and $NH_4^+$; with the proviso that when the polymer contains 0 wt % of monomer residues of residue B and 0 wt % of monomer residues of residue C, $R_2$ is —$CH_2CO_2R_5$ or —$CO_2R_5$, $R_5$ is (V) and Y is X;
$R_3$ is selected from H, methyl, phenyl, sulfonated phenyl, phenol, acetate, hydroxy, a fragment O—$R_1$, where $R_1$ is as defined previously, —$CO_2R_{12}$ and —$CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;
$R_8$ and $R_9$ are independently selected from hydrogen, methyl, ethyl and $C_3$-$C_4$ alkyl;
$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly ($C_2$-$C_4$ alkylene)$_b$ oxides; where b is an integer from 2 to 20.

2. The treated fiber substrate of claim 1, wherein the metal is silver.

3. The treated fiber substrate of claim 2, wherein the finish is non-electrically conductive.

4. The treated fiber substrate of claim 1, wherein the finish further comprises at least one binder material.

5. The treated fiber substrate of claim 1, wherein the treated fiber substrate exhibits a log kill rate for *Staphylococcus aureus* after 24 hour exposure in accordance with AATCC Test Method 100-1993 of at least 1.5, wherein said log kill rate is measured after at least 3 washes, wherein the washes are performed in accordance with the wash procedure as part of a modified AATCC Test Method 124-2001.

6. The treated fiber substrate of claim 1, wherein the treated fiber retains at least 50 wt % of the initial applied metal concentration after being subjected to 3 washes, wherein the washes are performed in accordance with the wash procedure set forth in AATCC Test Method 124-2001.

7. A material made using the treated fiber substrate of claim 1, wherein the material is selected from apparel, apparel interlining, upholstery, carpeting, padding, ceiling tiles, acoustical tiles, backing, wall coverings, roofing products, house wraps, insulation, bedding, wiping cloths, towels, gloves, rugs, floor mats, drapery, napery, textile bags, awnings, vehicle covers, boat covers, tents, agricultural coverings, geotextiles, automotive headliners, filtration media, dust masks, fiber fill, envelopes, tags, labels, diapers, feminine hygiene products, laundry aids, wound care products and medical care products.

8. A process for producing a treated fiber substrate comprising:
providing a fiber substrate;
providing a finish comprising at least one antimicrobial compound comprising a metal complexed with a polymer; wherein the metal is selected from copper, silver, gold, tin, zinc and combinations thereof; and, wherein the polymer comprises monomer residues selected from residue A, residue B, residue C and combinations thereof; with the proviso that the polymer contains no more than 99.5 wt % of monomer residues of residue B;
wherein residue A is

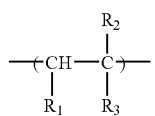

wherein residue B is

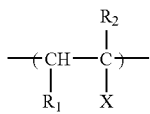

wherein residue C is

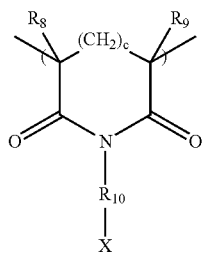

wherein
X is an unsaturated or aromatic heterocycle having at least one hetero atom selected from N, O and S;
c is 0 or 1;
$R_1$ is selected from H, $CH_3$ and $-CO_2R_4$; where $R_4$ is selected from H, $CH_3$, $C_2H_5$, a $C_3$-$C_{24}$ alkyl;
$R_2$ is selected from H, $CH_3$, $C_2H_5$, phenyl, $-CH_2CO_2R_5$ and $-CO_2R_5$; where $R_5$ is selected from (I)-(V),

H;  (I)

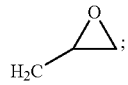  (II)

$-(CH_2CH(R_{11})O)_nH$;  (III)

$-(CH_2CH(R_{11})O)_nCOCH_2COCH_3$; and,  (IV)

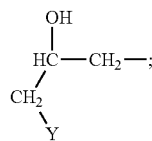  (V)

where $R_{11}$ is selected from H, methyl and phenyl; n is an integer from 1 to 20; Y is selected from OH, $SO_3Z$ and X; where Z is selected from H, sodium, potassium and $NH_4^+$; with the proviso that when the polymer contains 0 wt % of monomer residues of residue B and 0 wt % of monomer residues of residue C, $R_2$ is $-CH_2CO_2R_5$ or $-CO_2R_5$, $R_5$ is (V) and Y is X;

$R_3$ is selected from H, methyl, phenyl, sulfonated phenyl, phenol, acetate, hydroxy, a fragment $O-R_1$, where $R_1$ is as defined previously, $-CO_2R_{12}$ and $-CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;

$R_8$ and $R_9$ are independently selected from hydrogen, methyl, ethyl and $C_3$-$C_4$ alkyl;

$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly ($C_2$-$C_4$ alkylene)$_b$ oxides; where b is an integer from 2 to 20; and, applying the finish to at least a portion of a surface of the fiber substrate;

optionally, providing a binder material;

optionally, applying the binder material to at least a portion of the surface of the fiber substrate; and, optionally, drying the treated fiber substrate.

9. A process for producing a treated fiber substrate comprising:

providing a fiber substrate;

providing a finish comprising at least one antimicrobial compound comprising silver complexed with a polymer; wherein the polymer comprises monomer residues selected from residue A, residue B, residue C and combinations thereof; with the proviso that the polymer contains no more than 99.5 wt % of monomer residues of residue B;

wherein residue A is

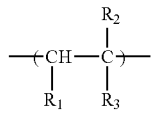

wherein residue B is

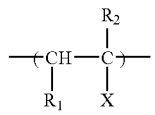

wherein residue C is

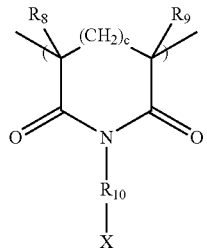

wherein
X is an unsaturated or aromatic heterocycle having at least one hetero atom selected from N, O and S;
c is 0 or 1;
$R_1$ is selected from H, $CH_3$ and $-CO_2R_4$; where $R_4$ is selected from H, $CH_3$, $C_2H_5$, a $C_3$-$C_{24}$ alkyl;
$R_2$ is selected from H, $CH_3$, $C_2H_5$, phenyl, $-CH_2CO_2R_5$ and $-CO_2R_5$; where $R_5$ is selected from (I)-(V),

H; (I)

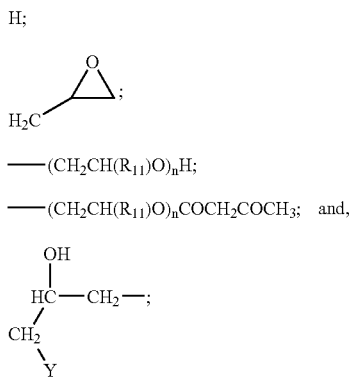
(II)

—(CH$_2$CH(R$_{11}$)O)$_n$H; (III)

—(CH$_2$CH(R$_{11}$)O)$_n$COCH$_2$COCH$_3$; and, (IV)

$$\begin{array}{c} \text{OH} \\ | \\ \text{HC—CH}_2\text{—}; \\ / \\ \text{CH}_2 \\ \backslash \\ \text{Y} \end{array}$$
(V)

where R$_{11}$ is selected from H, methyl and phenyl; n is an integer from 1 to 20; Y is selected from OH, SO$_3$Z and X; where Z is selected from H, sodium, potassium and NH$_4^+$; with the proviso that when the polymer contains 0 wt % of monomer residues of residue B and 0 wt % of monomer residues of residue C, R$_2$ is —CH$_2$CO$_2$R$_5$ or —CO$_2$R$_5$, R$_5$ is (V) and Y is X;

R$_3$ is selected from H, methyl, phenyl, sulfonated phenyl, phenol, acetate, hydroxy, a fragment O—R$_1$, where R$_1$ is as defined previously, —CO$_2$R$_{12}$ and —CONR$_6$R$_7$; where R$_6$ and R$_7$ are independently selected from H, methyl, ethyl, C(CH$_3$)$_2$CH$_2$SO$_3$Z, where Z is as defined previously, C$_3$-C$_8$ alkyl and a combined ring structure and R$_{12}$ is selected from H, CH$_3$, C$_2$H$_5$ and C$_3$-C$_{24}$ alkyl;

R$_8$ and R$_9$ are independently selected from hydrogen, methyl, ethyl and C$_3$-C$_4$ alkyl;

R$_{10}$ is selected from C$_1$-C$_8$ alkyl, C$_2$-C$_8$ alkenyl, C$_6$-C$_{10}$ unsaturated acyclic, C$_6$-C$_{10}$ cyclic, C$_6$-C$_{10}$ aromatic, C$_2$-C$_4$ alkylene oxide and poly (C$_2$-C$_4$ alkylene)$_b$ oxides; where b is an integer from 2 to 20;

applying the finish to at least a portion of a surface of the fiber substrate;

optionally, providing a binder material;

optionally, applying the binder material to at least a portion of the surface of the fiber substrate; and, optionally, drying the treated fiber substrate.

10. The process of claim 9, wherein the fiber substrate is selected from fibers, yarns and fabrics.

11. The treated fiber substrate of claim 1, wherein the polymer comprises a heterocyclic containing monomer and a non-heterocyclic containing monomer, and wherein the composition is light stable.

12. The treated fiber substrate of claim 11, wherein the metal is silver.

13. The treated fiber substrate of claim 12, wherein the finish is non-electrically conductive.

14. The treated fiber substrate of claim 11, wherein the finish further comprises at least one binder material.

15. The treated fiber substrate of claim 1, wherein the polymer comprises a copolymer of a heterocyclic containing monomer and a non-heterocyclic containing monomer, wherein the heterocyclic containing monomer is vinylimidazole and the non-heterocyclic containing monomer is butyl acrylate and wherein the ratio of the heterocyclic containing monomer to the non-heterocyclic containing monomer is between 95:5 to 5:95.

16. The treated fiber substrate of claim 11, wherein the treated fiber substrate exhibits a log kill rate for *Staphylococcus aureus* after 24 hour exposure in accordance with AATCC Test Method 100-1993 of at least 1.5, wherein said log kill rate is measured after at least 3 washes, wherein the washes are performed in accordance with the wash procedure as part of a modified AATCC Test Method 124-2001.

17. The treated fiber substrate of claim 11, wherein the treated fiber retains at least 50 wt % of the initial applied metal concentration after being subjected to 3 washes, wherein the washes are performed in accordance with the wash procedure set forth in AATCC Test Method 124-2001.

18. A material comprising the treated fiber substrate of claim 11, wherein the material is selected from apparel, apparel interlining, upholstery, carpeting, padding, ceiling tiles, acoustical tiles, backing, wall coverings, roofing products, house wraps, insulation, bedding, wiping cloths, towels, gloves, rugs, floor mats, drapery, napery, textile bags, awnings, vehicle covers, boat covers, tents, agricultural coverings, geotextiles, automotive headliners, filtration media, dust masks, fiber fill, envelopes, tags, labels, diapers, feminine hygiene products, laundry aids, wound care products and medical care products.

19. The process of claim 9, wherein the polymer comprises a heterocyclic containing monomer and a non-heterocyclic containing monomer, and wherein the composition is light stable.

* * * * *